(12) United States Patent
Baumgartner et al.

(10) Patent No.: US 10,119,097 B2
(45) Date of Patent: Nov. 6, 2018

(54) ORGANIC COMPOUNDS

(71) Applicant: GIVAUDAN SA, Vernier (CH)

(72) Inventors: Corinne Baumgartner, Faellanden (CH); Felix Flachsmann, Duebendorf (CH)

(73) Assignee: GIVAUDAN S.A., Vernier (CH)

( * ) Notice: Subject to any disclaimer, the term of this patent is extended or adjusted under 35 U.S.C. 154(b) by 17 days.

(21) Appl. No.: 15/516,828

(22) PCT Filed: Nov. 10, 2014

(86) PCT No.: PCT/EP2014/074191
§ 371 (c)(1),
(2) Date: Apr. 4, 2017

(87) PCT Pub. No.: WO2016/074699
PCT Pub. Date: May 19, 2016

(65) Prior Publication Data
US 2017/0298292 A1 Oct. 19, 2017

(51) Int. Cl.
*C11B 9/00* (2006.01)
*C11D 3/50* (2006.01)
*C07C 69/738* (2006.01)
*C07C 43/215* (2006.01)
*C07C 43/205* (2006.01)

(52) U.S. Cl.
CPC .......... *C11B 9/0061* (2013.01); *C07C 43/205* (2013.01); *C07C 43/215* (2013.01); *C07C 69/738* (2013.01); *C11B 9/003* (2013.01); *C11D 3/507* (2013.01)

(58) Field of Classification Search
CPC ..................................... C11B 9/0061
See application file for complete search history.

(56) References Cited

U.S. PATENT DOCUMENTS 5,527,769 A * 6/1996 Winter ............... C07C 33/20
424/76.4

FOREIGN PATENT DOCUMENTS

| WO | 2013045301 A1 | 4/2013 |
| WO | 2013113533 A1 | 8/2013 |
| WO | 2014180945 A1 | 11/2014 |

OTHER PUBLICATIONS

International Search Report and Written Opinion of the International Searching Authority for corresponding application PCT/EP2014/074191 dated Aug. 11, 2015.
G. Skouroumis, et al., "Synthesis of 1,3,4,5-Tetrahydro-2-Benzoxepin Derivatives as Conformationally Restricted Analogues of Cyclmenaldehyde-Type Compounds and as Intermediates for Highly Odour-Active Homologues", Helvetica Chimica Acta, Verlag Helvetica Chimica Acta, CH, vol. 79, No. 4, Jan. 1, 1996, pp. 1095-1109.

* cited by examiner

*Primary Examiner* — Arrie L Reuther
(74) *Attorney, Agent, or Firm* — Norris McLaughlin & Marcus PA

(57) ABSTRACT

A fragrance precursor represented by the formula 1

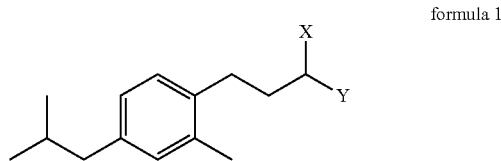

formula 1 wherein
X and Y together represent a double bond to a carbon atom bearing $R_1$ and $R_2$, with $R_1$=H, methyl, acetyl or $C_1$-$C_3$ alkoxycarbonyl (e.g. ethoxycarbonyl); and R2=phenyl optionally substituted with up to 3 (i.e. 0, 1, 2 or 3) groups selected from $C_1$-$C_4$ alkyl (e.g. methyl, ethyl, iso-propyl, tert-butyl), vinyl, hydroxy, $C_1$-$C_3$ alkoxy (e.g. ethoxy), and —O—$CH_2$—O—, e.g. $R_2$ is benzo[d][1,3]dioxol-5-yl, 4-methylphenyl, 4-methoxyphenyl, 4-vinylphenyl or 3-ethoxy-4-hydroxyphenyl or
R2=naphthyl, (naphthyl)methyl, 1,1,2,4,4,8-hexamethyl-1,2,3,4-tetrahydronaphthalen-7-yl, or 1,1,2,4,4,-pentamethyl-1,2,3,4-tetrahydronaphthalen-7-yl or
R2=COR3, wherein R3 is H, C1-C10 alkoxy (e.g. ethoxy, 1-(3,3-dimethylcyclohexyl)ethoxy), C1-C4 alkyl (e.g. methyl, ethyl, propyl, iso-propyl, tert-butyl), e.g. R2 is formyl, acetyl, ethoxycarbonyl, 1-(3,3-dimethylcyclohexyl)ethoxycarbonyl; or wherein
X is OR4, with R4 being H or alkyl, and
Y is OR5, with R5 being alkyl,
useful as a perfume ingredient.

18 Claims, No Drawings

ORGANIC COMPOUNDS

This is an application filed under 35 U.S.C. 371 of PCT/EP2014/074191 filed 10 Nov. 2014. The present application claims all available priority benefit to the foregoing application, and also herein incorporates by reference the entirety of its disclosure.

The present invention relates to fragrance precursors. These fragrance precursors are able to release 3-(4-isobutyl-2-methylphenyl)propanal. Furthermore, the invention relates to the use of such fragrance precursors in perfume preparations. In particular, the invention relates to fragrance precursors or perfume preparations containing said precursors that release fragrance with muguet (lily of the valley) odour characteristics. Still more particularly, the invention relates to said perfume preparations that contain no, or substantially no, Lilial™. The invention further relates to methods of making said perfume precursors and perfume preparations, as well as the use of said perfume precursors and perfume preparations in fine fragrances and consumer products, such as personal care and household care products. The invention also relates to said fine fragrances and consumer products containing said perfume precursors and perfume preparations.

Compounds having muguet odour characteristics are very sought after as perfume ingredients. These compounds are important ingredients in floral bases and can act as harmonizers across many types of fragrance creations. Compounds of this type are used widely in personal care and consumer care products, as well as in fine perfumery, to generate pleasant odours or to mask unpleasant odours.

An excellent perfume ingredient widely valued for its muguet odour note is Lilial™ or 3-(4-tert-butylphenyl)-2-methylpropanal (CAS 80-54-6). This compound has found wide use in fine perfumery as well as in personal and household care products. However, its use is controversial in view of recent findings that it exhibits toxic effects on the reproductive organs of male rats and dogs. No effects were found in studies with mice, guinea-pigs and primates, nevertheless, under the Global Harmonized System (GHS) classification system this compound is classified as a CMR2 material. For CMR category 2 materials, it is necessary to establish that quantities proposed for use are harmless to consumers. In view of the regulatory status of Lilial™ it is being replaced with other perfume ingredients.

Recently, applicant has found a novel compound 3-(4-isobutyl-2-methylphenyl)propanal that can be employed as a perfume ingredient in perfume compositions and fine fragrances and consumer products. The novel compound possesses desirable muguet odour characteristics and may be perceived and recognised by perfumers as being very reminiscent of the odour of Lilial™ and so can serve as a simple replacement for Lilial™. The novel compound does not attract the regulatory concerns associated with Lilial™. Details of this invention are disclosed in patent application PCT/EP2014/059427, which is hereby incorporated by reference.

Perfumed products such as cleaning or laundry products comprising Lilial™ are well-known in the art.

However, it is known that fragrances can be altered through degradation caused by interaction with air or when incorporated in certain consumer product bases, where alkalinity, acidity, the presence of oxidizing agents, such as hypochlorite salts, or other base components may lead to chemical degradation of the fragrance. In addition, volatile fragrances tend to be dissipated with time. Furthermore, when used in cleaning or laundry products, the deposition of the fragrance on a treated substrate is diminished by the washing and/or rinsing procedure.

Nevertheless, it is desired by consumers to have products that can be stored over time and still giving a constant perfume impression. In particular, the impact of volatile components is to be retained. Furthermore, it is desired that such products create a long-lasting pleasing fragrance slowly emitting from the treated substrate over time.

Therefore, it is an objective of the present invention to provide a system which is capable of releasing the above mentioned Lilial™ type fragrance constantly over time and providing a long-lasting release of said fragrance.

It is another objective of the present invention to increase the substantivity of 3-(4-isobutyl-2-methyl phenyl)propanal, in particular in consumer product applications, especially in the so-called rinse off applications, like fabric softener or conditioner, as well as in hair shampoo or fabric detergents.

Applicant has found that derivatives of 3-(4-isobutyl-2-methylphenyl)propanal can serve as fragrance precursors of 3-(4-isobutyl-2-methylphenyl)propanal. These fragrance precursors provide a delayed release of 3-(4-isobutyl-2-methylphenyl)propanal over a longer period of time than by the use of the fragrance itself.

Accordingly, the invention provides in a first aspect a compound represented by formula 1

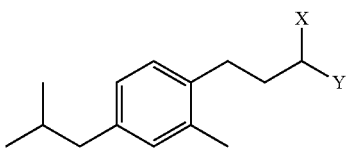

formula 1 wherein

X and Y together represent a double bond to a carbon atom which is bearing $R_1$ and $R_2$, with $R_1$=H, methyl, acetyl or $C_1$-$C_3$ alkoxycarbonyl (e.g. ethoxycarbonyl); and $R_2$=phenyl optionally substituted with up to 3 (i.e. 0, 1, 2 or 3) groups selected from $C_1$-$C_4$ alkyl (e.g. methyl, ethyl, iso-propyl, tert-butyl), vinyl, hydroxy, $C_1$-$C_3$ alkoxy (e.g. ethoxy), and —O—CH$_2$—O—, e.g. $R_2$ is benzo[d][1,3]dioxol-5-yl, 4-methylphenyl, 4-methoxyphenyl, 4-vinyl-phenyl or 3-ethoxy-4-hydroxyphenyl or $R_2$=naphthyl, (naphthyl)methyl, 1,1,2,4,4,8-hexamethyl-1,2,3,4-tetrahydronaphthalen-7-yl, or 1,1,2,4,4,-pentamethyl-1,2,3,4-tetrahydronaphthalen-7-yl or $R_2$=COR$_3$, wherein $R_3$ is H, $C_1$-$C_{10}$ alkoxy (e.g. ethoxy, 1-(3,3-dimethylcyclohexyl)ethoxy), $C_1$-$C_4$ alkyl (e.g. methyl, ethyl, propyl, iso-propyl, tert-butyl), e.g. $R_2$ is formyl, acetyl, ethoxycarbonyl, 1-(3,3-dimethylcyclohexyl)ethoxycarbonyl;

or wherein

X is OR$_4$, with $R_4$ being H, Me or a branched or linear, saturated or unsaturated $C_2$-$C_5$ alkyl or alkenyl residue (e.g. ethyl, propyl, iso-propyl, tert-butyl), and Y is OR$_5$, with $R_5$ being Me or a branched or linear, saturated or unsaturated $C_2$-$C_5$ alkyl or alkenyl residue (e.g. ethyl, propyl, iso-propyl, tert-butyl).

The compounds represented by formula 1 as described above are suitable fragrance precursors.

The said fragrance precursors are able to release 3-(4-isobutyl-2-methylphenyl)propanal, a compound with substantially similar odour characteristics and performance characteristics as Lilial™. The precursors provide an improved fragrance intensity and a long-lasting release (also known as substantivity) of 3-(4-isobutyl-2-methylphenyl)propanal.

According to the present invention, a fragrance precursor is a substance that is not itself a final fragrance, but which, in particular circumstances will break down to give at least one desired fragrant substance. The fragrance precursor will release the desired fragrance for example by hydrolysis with air moisture or water. The release can also be caused by exposure to light or oxygen, pH change and enzymatic activity.

The fragrance precursor itself can be odourless. Alternatively, the precursor may be an odorant on its own.

Furthermore, the precursors are substantially odourless or have pleasant odour characteristics that may improve odour properties of the overall fragrance, respectively. It is important that the odour properties of the overall fragrance are not affected, or are not adversely affected, by the presence of the reaction product.

In one of the aspects of the invention, it is preferred that the fragrance precursor is a compound represented by formula 2

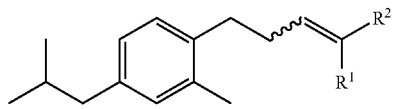

formula 2 wherein $R_1$=H, methyl, acetyl or $C_1$-$C_3$ alkoxycarbonyl (e.g. ethoxycarbonyl); and $R_2$=phenyl optionally substituted with up to 3 (i.e. 0, 1, 2 or 3) groups selected from $C_1$-$C_4$ alkyl (e.g. methyl, ethyl, iso-propyl, tert-butyl), vinyl, hydroxy, $C_1$-$C_3$ alkoxy (e.g. ethoxy), and —O—CH$_2$—O—, e.g. $R_2$ is benzo[d][1,3]dioxol-5-yl, 4-methylphenyl, 4-methoxyphenyl, 4-vinylphenyl or 3-ethoxy-4-hydroxyphenyl or $R_2$=naphthyl, (naphthyl)methyl, 1,1,2,4,4,8-hexamethyl-1,2,3,4-tetrahydronaphthalen-7-yl, or 1,1,2,4,4,-pentamethyl-1,2,3,4-tetrahydronaphthalen-7-yl or $R_2$=COR$_3$, wherein $R_3$ is H, $C_1$-$C_{10}$ alkoxy (e.g. ethoxy, 1-(3,3-dimethylcyclohexyl)ethoxy), $C_1$-$C_4$ alkyl (e.g. methyl, ethyl, propyl, iso-propyl, tert-butyl), e.g. $R_2$ is formyl, acetyl, ethoxycarbonyl, 1-(3,3-dimethylcyclohexyl)ethoxycarbonyl;

and wherein the wavy bond is indicating an unspecified configuration of the adjacent double bond, so that the compound has an E- or a Z-configuration, or is a mixture of E/Z-isomers.

The described fragrance precursor represented by formula 2 may be synthesized in one step from 3-(4-isobutyl-2-methyl phenyl)propanal.

For example, the fragrance precursor represented by formula 2 can be prepared via a Wittig reaction with 3-(4-isobutyl-2-methylphenyl)propanal and a phosphorous ylide derived in situ from a benzyltriphenyl-phosphonium-halogen salt.

In another embodiment of the invention, the fragrance precursor represented by formula 2 can be derived from a Knoevenagel- or Aldol-condensation reaction with 3-(4-isobutyl-2-methylphenyl)propanal and an alkyl acetoacetate, a dialkyl malonate or acetone under reaction conditions known in the art.

It is preferred to use a fragrance precursor as a prepared compound represented by formula 2 in a perfume mixture. However, in another aspect of the invention, it is possible to form said fragrance precursor directly in the perfume mixture by adding the starting compounds into the perfume mixture. For example, after addition of 3-(4-isobutyl-2-methylphenyl)propanal and ethyl acetoacetate into a perfume mixture, the corresponding fragrance precursor ethyl 2-acetyl-5-(4-isobutyl-2-methylphenyl)pent-2-enoate, that is a compound represented by formula 2, is formed.

In another of the aspects of the invention, it is preferred that the fragrance precursor is a compound represented by formula 3

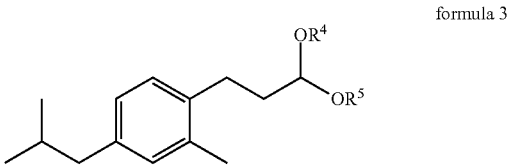

formula 3 with $R_4$ being H, Me or a branched or linear, saturated or unsaturated $C_2$-$C_5$ alkyl or alkenyl residue (e.g. ethyl, propyl, iso-propyl, tert-butyl), and $R_5$ being Me or a branched or linear, saturated or unsaturated $C_2$-$C_5$ alkyl or alkenyl residue (e.g. ethyl, propyl, iso-propyl, tert-butyl).

For example, compounds of formula 3 may be synthesized by treating 3-(4-isobutyl-2-methylphenyl)propanal with suitable alcohols HOR$_4$ and/or HOR$_5$ under acidic conditions at reflux.

Such acetals or hemi-acetals represented by formula 3 can be prepared and added to a perfume mixture. In a further aspect of the invention, they may be formed directly in the perfume mixture by addition of the starting compounds to the perfume mixture.

In one particular aspect of the invention, the fragrance precursors represented by formula 1 are substantially odourless or have pleasant odour characteristics that may improve odour properties of the overall fragrance, respectively. It is important that the odour properties of the overall fragrance are not affected, or are not adversely affected, by the presence of the reaction product.

In another of its aspects, the invention provides the use of the described fragrance precursors as a perfume ingredient.

In particular, the precursor as perfume ingredient can release an ingredient with muguet odour characteristics.

As such, and in contradistinction to the prior art proposals related to Lilial™ replacement based on mixtures of known ingredients, the present invention provides a precursor that can release a single fragrance compound for a Lilial™ replacement. Such a replacement by a single fragrance might be cost-effective and convenient for a perfumer.

The invention provides in another of its aspects the use of the described fragrance precursor in a perfume composition that is able to release 3-(4-isobutyl-2-methylphenyl)propanal as a replacement for aryl-substituted alkanals, more particularly aryl-substituted propanal odourants that are unsubstituted on the aryl ring at a position ortho to the substituent bearing the aldehyde functionality, in particular Lilial™.

The compound released by the precursor of the present invention is not susceptible to enzymatic degradation to its benzoic acid derivative. This was indeed a very surprising result considering the close structural similarity to Lilial ™.

The applicant's surprising discovery that an aryl-substituted alkanal containing a methyl substituent on the ring at a position ortho to the group bearing the aldehyde functionality is not susceptible to enzymatic degradation to its benzoic acid derivative, provides an insight heretofore not known in the art, and allows perfumers to formulate with a compound that although being structurally similar to Lilial™ (and therefore possessing remarkably similar olfactive properties as these compounds), nevertheless does not raise similar regulatory issues.

In order to study in vitro metabolism in rat hepatocytes Lilial™ and the compound released by the precursors of the present invention are incubated in presence of rat hepatocytes in suspension. Decrease of Lilial™ and the compound released by the precursor of the present invention, and formation of the corresponding benzoic acid derivative may be analysed by GC-MS.

Accordingly, in another aspect of the present invention there is provided a fragrance precursor that is able to release 3-(4-isobutyl-2-methylphenyl)propanal that forms no, or substantially no, corresponding benzoic acid derivative when incubated with hepatocytes isolated from rats. By "substantially no benzoic acid derivative" is meant that the concentration of said derivative is below the limit of detection, i.e. <1%. As such, the fragrance precursor releasing 3-(4-isobutyl-2-methylphenyl)propanal provides perfumers with an eminently suitable surrogate for the valuable yet problematic Lilial™.

In another aspect of the invention there is provided a method of imparting a muguet odour characteristic to a perfume composition, said method comprising the step of incorporating a fragrance precursor that is able to release 3-(4-isobutyl-2-methylphenyl)propanal into said perfume composition.

In yet another aspect of the invention there is provided a perfume composition comprising a fragrance precursor represented by formula 1 that is able to release 3-(4-isobutyl-2-methylphenyl)propanal into said perfume composition.

In yet another aspect of the invention there is provided a perfume composition possessing muguet odour characteristics comprising a fragrance precursor represented by formula 1 that is able to release 3-(4-isobutyl-2-methylphenyl)propanal.

In yet another aspect of the present invention there is provided a perfume composition comprising a fragrance precursor that is substantially free of aryl-substituted propanal odourants that are unsubstituted on the aryl ring at a position ortho to the substituent bearing the aldehyde functionality, in particular Lilial™.

A perfume composition according to the present invention can be made up entirely by the fragrance precursor represented by formula 1. However, a perfume composition may also contain, in addition to the said fragrance precursor, one or more additional perfume ingredients.

The fragrance precursor according to formula 1 may be present in a perfume composition in any amount depending on the particular olfactive effect that a perfumer wishes to achieve. In a particular embodiment of the present invention, a perfume composition of the present invention may contain the said fragrance precursor in an amount of 0.1 to 100% by weight of said composition.

It is particularly preferred, that the perfume composition further comprises 3-(4-isobutyl-2-methylphenyl)propanal. The mixture of the fragrance and a precursor releasing said fragrance ensures a constant and long-lasting fragrance impression over time.

The perfume composition may further comprise additional perfume ingredients. If one or more additional perfume ingredients are employed, they may be selected from any known perfume ingredients or from their precursor systems, respectively.

In particular, said perfume ingredients that may be employed in a perfume composition according to the invention include (E/Z)-9-hydroxy-5,9-dimethyldec-4-enal, 6-methoxy-2,6-dimethylheptan-1-al (methoxymelonal), 5,9-dimethyl-4,8-decadienal (geraldehyde), beta-methyl-3-(1-methylethyl)benzenepropanal (florhydral), octahydro-8,8-dimethylnaphthalene-2-carbaldehyde (cyclomyral), alpha-methyl-1,3-benzodioxole-5-propionaldehyde (helional), 5-methyl-2-(1-methylbutyl)-5-propyl-1,3-dioxan (Troenan), 3-(o-ethyl phenyl)-2,2-dimethylpropionaldehyde (floralozone), farnesol, 3,7,11-trimethyldodeca-1,6,10-trien-3-ol, optionally as an isomeric mixture (nerolidol), 2-methyl-4-phenylbutan-2-ol (dimethylphenylethylcarbinol), cis-4-(isopropyl)cyclohexanemethanol (mayol), 1-(1-hydroxyethyl)-4-(1-methylethyl)cyclohexane (optionally as a mixture of the diastereoisomers) (mugetanol), (4-methyl-3-pentenyl)cyclohexenecarbaldehyde (citrusal), cyclohexyl salicylate, hexyl salicylate, benzyl salicylate, amyl salicylate, 3-(p-(2-methylpropyl)phenyl)-2-methylpropionaldehyde (silvial), 3-p-cumenyl-2-methylpropionaldehyde (cyclamenaldehyde), mixtures of: cis-tetrahydro-2-isobutyl-4-methylpyran-4-ol; trans-tetrahydro-2-isobutyl-4-methylpyran-4-ol; (florol), triethyl citrate and dipropylene glycol.

Said perfume ingredients may additionally include Amyl Salicylate (2050-08-0); Aurantiol® (89-43-0); Benzyl Salicylate (118-58-1); Cis-3-hexenyl Salicylate (65405-77-8); Citronellyl Oxyacetaldehyde (7492-67-3); Cyclemax (7775-00-0); Cyclohexyl Salicylate (25485-88-5); Cyclomyral® (68738-94-3); Citronellol (106-22-9); Geraniol (106-24-1); Cyclopentol Hc 937165 (84560-00-9); Cymal (103-95-7); Dupical (30168-23-1); Ethyl Linalool (10339-55-6); Floral Super (71077-31-1); Florhydral® (125109-85-5); Florol® (63500-71-0); Gyrane (24237-00-1); Hexyl Salicylate (6259-76-3); Helional™ (1205-17-0); Hydroxycitronellal (107-75-5); Linalool (78-70-6); Lyral® (31906-04-4); Majantol® (103694-68-4); Mayol® (13828-37-0); Melafleur (68991-97-9); Melonal (106-72-9); Mugetanol (63767-86-2); Muguesia (56836-93-2); Muguet alcohol (13351-61-6); Verdantiol (91-51-0); Peonile® (10461-98-0); Phenoxanol® (55066-48-3); Rossitol® (215231-33-7); Silvial® (6658-48-6); Suzural (6658-48-6); Muguol® (18479-57-7); Tetrahydro Linalol (78-69-3); Acalea (84697-09-6); Dihydro Iso Jasmonate (37172-53-5); Hexyl Cinnamic Aldehyde (101-86-0); Hedione® (24851-98-7); Acetoin (513-86-0); Adoxal (141-13-9); Aldolone® (207228-93-1); AMBROCENIDE® (211299-54-6); Ambroxan (3738-00-9); Azurone® (362467-67-2); Bacdanol® (28219-61-6); Calone 1951® (28940-11-6); Cetalox® (3738-00-9); Cinnamic alcohol (104-54-1); Citral (5392-40-5); Cyclabute (67634-20-2); Cyclacet™ (5413-60-5); Cycleprop™ (17511-60-3); Cyclohexadecanolide (109-29-5); Cyclohexadecenone (3100-36-5); Cyclopentadecanone (507-72-7); Delta Damascone (57378-68-4); Ebanol® (67801-20-1); Elintaal Forte (40910-49-4); Ethyl Vanillin (121-32-4); Ethylene Brassylate (105-95-3); Exaltenone 942008 (14595-54-1); Exaltolide Total 935985 (106-02-5); Floralozone (67634-14-4); Fructalate (72903-27-6); Gamma Decalactone (706-14-9); Habanolide (111879-80-2); Helvetolide® (141773-73-1); Hexamethylindanopyran (1222-05-5); Hydroxyambran® (118562-73-5); Iso E Super® (54464-57-2); Iso Hexenyl Cyclohexenyl Carboxaldehyde (37677-14-8); Jasmal (18871-14-2); Javanol® (198404-98-

7); Lauric Aldehyde (112-54-9); Mefranal (55066-49-4); Muscenone (63314-79-4); Tonalid® (1506-02-1); Nectaryl® (95962-14-4); Norlim Banol (70788-30-6); Para Hydroxy Phenyl Butanone (5471-51-2); Pino Acetaldehyde (33885-51-7); Romandolide® (236391-76-7); Sanjinol (28219-61-6); Silvanone® Supra (109-29-5/507-72-7); Terpineol (8000-41-7); Vanillin (121-33-5); and Velvione® (37609-25-9), wherein, the figures in parentheses are CAS numbers.

A perfume composition need not be limited to the perfume ingredients listed above. Other perfume ingredients commonly used in perfumery may be employed, for example any of those ingredients described in "Perfume and Flavour Chemicals", S. Arctander, Allured Publishing Corporation, 1994, IL, USA, which is incorporated herein by reference, including essential oils, plant extracts, absolutes, resinoids, odourants obtained from natural products and the like.

The perfume ingredients contained in said perfume compositions are described above, but of course, the perfume mixture may not be limited to the stated ingredients. In particular, perfume compositions may comprise adjuvants that are commonly employed in perfume compositions. The term "adjuvants" refers to ingredients that might be employed in a perfume composition for reasons not specifically related to the olfactive performance of said composition. For example, an adjuvant may be an ingredient that acts as an aid to processing a perfume ingredient or ingredients, or a composition containing said ingredient(s), or it may improve handling or storage of a perfume ingredient or composition containing same. It might also be an ingredient that provides additional benefits such as imparting colour or texture. It might also be an ingredient that imparts light resistance or chemical stability to one or more ingredients contained in a perfume ingredient or composition containing same. A detailed description of the nature and type of adjuvants commonly used in perfume compositions containing same cannot be exhaustive, but it has to be mentioned that said ingredients are well known to a person skilled in the art. Examples of adjuvants include solvents and co-solvents; surfactants and emulsifiers; viscosity and rheology modifiers; thickening and gelling agents; preservative materials; pigments, dyestuffs and colouring matters; extenders, fillers and reinforcing agents; stabilisers against the detrimental effects of heat and light, bulking agents, acidulants, buffering agents and antioxidants.

Furthermore, any one or more of the perfume ingredients or adjuvants employed in the present invention might be formulated in a delivery vehicle if desired to provide a desired effect. Delivery vehicles may include encapsulates. Alternatively, a delivery vehicle may be in the form of a solid support, e.g. a polymeric support material onto which one or more perfume ingredients or adjuvants may be chemically or physically bound. Still further, one or more perfume ingredients or adjuvants may be dissolved or dispersed in a matrix material, which serves to control the rate at which said ingredient or ingredients emanates therefrom. In yet an alternative embodiment, one or more ingredients or adjuvants may be supported on a porous substrate, such as a cyclodextrin or a zeolite or other inorganic material. In a still further embodiment, one or more perfume ingredients may be provided in the form of a pro-perfume or precursor, which will react in a suitable environment to release the perfume ingredient in a controlled manner.

Having regard to the foregoing, it will be appreciated that a perfume composition may be at least partly in solid form, in gel form, in foam form and/or liquid form. If it is present in solid form, it then it may take the form of granules, powders or tablets.

The fragrance precursor or perfume compositions described herein, may be employed to add a characteristic odour, in particular a muguet odour, to all manner of personal care and household care compositions that will be released with time.

According to another aspect of the present invention there is provided a method of imparting muguet odour characteristics to a composition comprising the step of adding to said composition a fragrance precursor that is able to release 3-(4-isobutyl-2-methylphenyl)propanal or a perfume composition containing said fragrance precursor.

A fragrance precursor as a perfume ingredient, or when used in perfume compositions can generate particularly substantive and long-lasting muguet odour characteristics.

The compound released by the precursor, 3-(4-isobutyl-2-methylphenyl)propanal, is a particularly impactful perfume ingredient. The impact that a perfume ingredient exerts is related to its Odour Value. Odour Value is the rat of vapour pressure to detection threshold concentration.

Consumer products such as personal and household care compositions include, but are not limited to a textile treatment product, an ironing aid, a cleaning cloth, a laundry detergent, a cleaning product, in particular, for hard and/or soft surfaces, a household cleaner, a care product, a wash care product, a laundry care product, a room fragrancer, and air freshener, a conditioner, a colorant, a fabric conditioner, a conditioning substrate, a pharmaceutical, a crop protection product, a polish, a food, a cosmetic product, a fertilizer, a building material, an adhesive, a bleach, a decalcifier, an autocare product, floorcare product, cookercare product, leathercare product or furniture care product, a scourer, a disinfectant, a fragrancer, a mold remover and/or a precursor of the aforementioned products.

The skilled person is fully aware of the applicability of perfume ingredients, and compositions to personal and house hold care compositions and a very detailed description of such compositions is not warranted here. However, specific compositions that can be mentioned include cleaning compositions; autocare compositions; Cosmetic compositions; textile treatment compositions; and air freshener and air care compositions.

Cleaning products include:

Toilet cleaners or lavatory cleaners, in other words, products for cleaning lavatory bowls and urinals, these products being supplied preferably in the form of powders, blocks, tablets or liquids, preferably gels. Besides other typical ingredients such as surfactants, they generally include organic acids e.g., citric acid and/or lactic acid) or sodium hydrogen sulfate, amidosulfuric acid or phosphoric acid for removing limescale or urine scale;

Pipe-cleaning products or drain cleaners. These are typically strongly alkaline products which serve in general to remove pipe blockages comprising organic materials-such as hair, fat, food residues, soap deposits, and the like. Additions of Al powder or Zn powder may serve for the formation of $H_2$ gas with an effervescence effect. Possible ingredients are commonly alkalis, alkaline salts, oxidizing agents, and neutral salts. Supply forms in powder form preferably also include sodium nitrate and sodium chloride. Pipe-cleaning products in liquid form may preferably also include hypochlorite. There are also enzyme-based drain cleaners as well. Acidic products are likewise possible;

Universal or all-purpose or general-purpose cleaners. These are cleaners which can be used universally for all hard surfaces in the household and in commerce that can be wiped down wet or damp. Generally speaking, they are neutral or slightly alkaline or slightly acidic products, especially liquid products. All-purpose or general-purpose cleaners generally contain surfactants, builders, solvents and hydrotropes, dyes, preservatives, and the like;

All-purpose cleaners with special disinfectant properties. They additionally include active antimicrobial ingredients (e.g., aldehydes, alcohols, quaternary ammonium compounds, amphoteric surfactants, triclosan);

Sanitary cleaners. These are products for cleaning in bath and toilet. The alkaline sanitary cleaners are used preferably for removing fatty soiling, whereas the acidic sanitary cleaners are employed in particular, for removing limescale. Sanitary cleaners advantageously also have a considerable disinfectant action, particularly the strongly alkaline sanitary cleaners that contain chlorine;

Oven cleaners or grill cleaners which may be supplied in the form of gels or foam sprays. They generally serve for removing burnt-on or carbonized food residues. Oven cleaners are preferably given a strongly alkaline formulation using, for example, sodium hydroxide, sodium metasilicate, 2-aminoethanol. In addition they generally contain anionic and/or nonionic surfactants, water-soluble solvents, and, in some cases, thickeners such as polycarboxylates and carboxymethylcellulose;

Metal polishes. These are cleaners for particular types of metal such as stainless steel or silver. Stainless steel cleaners preferably contain, besides acids (preferably up to 3% by weight, e.g., citric acid, lactic acid), surfactants (in particular, up to 5% by weight, preferably nonionic and/or anionic surfactants), and water, solvents as well (preferably up to 15% by weight) to remove fatty soiling, and also further compounds such as thickeners and preservatives. Very fine polishing structures are included, furthermore, in products for preferably bright stainless steel surfaces. Silver polishes, in turn, may be provided in an acidic formulation. In particular, for removing black deposits of silver sulfide they contain, preferably, complexing agents (e.g., thiourea, sodium thiosulfate). Typical supply forms are polishing cloths, dipping baths, pastes, and liquids. Dark discolorations (oxide layers) are removed using copper cleaners and nonferrous-metal cleaners (e.g., for brass and bronze). They generally have a weakly alkaline formulation (preferably with ammonia) and in general contain polishing agents and also, preferably, ammonium soaps and/or complexing agents;

Glass cleaners and window cleaners. These products serve preferably to remove dirt, especially greasy dirt, from glass surfaces. Preferably they contain compounds such as anionic and/or nonionic surfactants (in particular, up to 5% by weight), ammonia and/or ethanolamine (in particular, up to 1% by weight), ethanol and/or 2-propanol, glycol ethers (in particular, 10-30% by weight), water, preservatives, dyes, anti-misting agents and the like; and Special-purpose cleaning products, examples being those for glass-ceramic hobs, and also carpet cleaners and stain removers.

Autocare products include:
Paint preservers, paint polishes, paint cleaners, wash preservers, shampoos for auto washing, auto-wash and wax products, polishes for trim metals, protective films for trim metals, plastics cleaners, tar removers, screen cleaners, engine cleaners, and the like.

Cosmetic products include:
(a) cosmetic skincare products, especially bath products, skin washing and cleansing products, skincare products, eye makeup, lip care products, nail care products, intimate care products, foot care products;
(b) cosmetic products with specific effects, especially sunscreens, tanning products, de-pigmenting products, deodorants, antiperspirants, hair removers, shaving products, perfumes;
(c) cosmetic dental-care products, especially dental and oral care products, tooth care products, cleaners for dental prostheses, adhesives for dental prostheses; and
(d) cosmetic hair care products, especially hair shampoos, hair care products, hair setting products, hair-shaping products, and hair coloring products.

Textile treatment products include:
Detergents or fabric conditioners, for example, in either liquid or solid form.

Air fresheners and room fragrancers include:
Products that contain preferably volatile and usually pleasant-smelling compounds which advantageously can even in very small amounts mask unpleasant odours. Air fresheners for living areas contain, in particular, natural and synthetic essential oils such as pine needle oils, citrus oil, eucalyptus oil, lavender oil, and the like., in amounts for example of up to 50% by weight. As aerosols they tend to contain smaller amounts of such essential oils, by way of example less than 5% or less than 2% by weight, but additionally include compounds such as acetaldehyde (in particular, <0.5% by weight), isopropyl alcohol (in particular, <5% by weight), mineral oil (in particular, <5% by weight), and propellants. Other presentation forms include sticks and blocks. They are produced typically using a gel concentrate comprising essential oils. It is also possible to add formaldehyde (for preservation) and chlorophyll (preferably <5% by weight), and also further ingredients. Air fresheners are not, however, restricted to living spaces, but may also be intended for autos, cupboards, dishwashers, refrigerators or shoes, and even their use in vacuum cleaners is a possibility. In the household (e.g., in cupboards), for example, in addition to the odour improvers, disinfectants as well are employed, containing preferably compounds such as calcium phosphate, talc, stearin, and essential oils, these products taking the form, for example, of sachets.

Consumer product compositions referred to hereinabove, particularly those for use in washing or cleaning applications may contain one or more of the following substances:

Builder substances, surfactants, enzymes, bleaching agents, such as preferably organic and/or inorganic peroxygen compounds, peroxygen activators, water-miscible organic solvents, sequestering agents, electrolytes, pH regulators, thickeners, and further adjuvants such as soil release active substances, optical brighteners, graying inhibitors, color transfer inhibitors, foam regulators, and dyes.

Surfactants include anionic surfactants, nonionic surfactants, and mixtures thereof, but also cationic surfactants, are appropriate. Suitable nonionic surfactants are, in particular, ethoxylation and/or propoxylation products of alkyl glycosides and/or of linear or branched alcohols each having 12 to 18 carbon atoms in the alkyl portion and 3 to 20, by preference 4 to 10, alkyl ether groups. Also usable are corresponding ethoxylation and/or propoxylation products of N-alkylamines, vicinal diols, fatty acid esters and fatty acid amides that correspond, in terms of the alkyl portion, to the aforesaid long-chain alcohol derivatives, and of alkylphenols having 5 to 12 carbon atoms in the alkyl residue.

Suitable anionic surfactants include soaps, and those that contain sulfate or sulfonate groups having preferably alkali ions as cations. Soaps include alkali salts of the saturated or unsaturated fatty acids having 12 to 18 carbon atoms. Such fatty acids can also be used in incompletely neutralized form. Included among the usable surfactants of the sulfate type are the salts of the sulfuric acid semi-esters of fatty alcohols having 12 to 18 carbon atoms, and the sulfated products of the aforesaid nonionic surfactants having a low degree of ethoxylation. Included among the usable surfactants of the sulfonate type are linear alkylbenzenesulfonates having 9 to 14 carbon atoms in the alkyl portion, alkanesulfonates having 12 to 18 carbon atoms, and olefinsulfonates having 12 to 18 carbon atoms that are produced upon reaction of corresponding monoolefins with sulfur trioxide, as well as alpha-sulfofatty acid esters that are produced upon sulfonation of fatty acid methyl or ethyl esters.

Cationic surfactants include esterquats and/or the quaternary ammonium compounds (QACs). QACs may be produced by the reaction of tertiary amines with alkylating agents such as methyl chloride, benzyl chloride, dimethyl sulfate, dodecyl bromide, but also ethylene oxide. The alkylation of tertiary amines having a long alkyl residue and two methyl groups occurs particularly easily, and the quaternization of tertiary amines having two long residues and one methyl group can also be carried out using methyl chloride under mild conditions. Amines that possess three long alkyl residues or hydroxy-substituted alkyl residues have low reactivity, and are quaternized, for example, using dimethyl sulfate. Suitable QACs are, for example, benzalkonium chloride (N-alkyl-N,N-dimethylbenzylammonium chloride), benzalkon B (m,p-dichlorobenzyldimethyl-C12-alkylammonium chloride), benzoxonium chloride (benzyl-dodecyl-bis(2-hydroxyethylpammonium chloride), cetrimonium bromide (N-hexadecyl-N,N-trimethylammonium bromide), benzetonium chloride (N,N -di methyl-N-[2-[2-[p-(1,1,3,3-tetramethylbutyl)phenoxy]ethoxy]ethyl]benzylammonium chloride), dialkyldimethylammonium chlorides such as di-n-decyldimethylammonium chloride, didecyldimethylammonium bromide, dioctyldimethylammonium chloride, 1-cetylpyridinium chloride, and thiazoline iodide, as well as mixtures thereof. Preferred QACs are the benzalkonium chlorides having C8 to C22 alkyl residues, in particular C12 to C14 alkylbenzyldimethylammonium chloride.

Esterquats include the commercially available methylhydroxyalkyldialkoyl-oxyalkylammonium methosulfates marketed by the Stepan company under the trademark Stepantex™, or the products of Cognis Deutschland GmbH known under the trade name Dehyquat™, or the Rewoquat™ products of Goldschmidt-Witco.

Surfactants may be employed in amounts of 5 wt % to 50 wt % in a consumer product of the present invention.

Builders include the water-soluble and/or water-insoluble, organic and/or inorganic builders. In particular, they include the water-soluble organic builder substances are polycarboxylic acids, more particularly citric acid and sugar acids, monomeric and polymeric a minopolycarboxylic acids, in particular methylglycinediacetic acid, nitrilotriacetic acid, and ethylenediaminetetraacetic acid, as well as polyaspartic acid, polyphosphonic acids, in particular a minotris(methylenephosphonic acid), ethylenediaminetetrakis(methylenephosphonic acid), and 1-hydroxyethane-1,1-diphosphonic acid, polymeric hydroxy compounds such as dextrin, as well as polymeric (poly)carboxylic acids, polymeric acrylic acids, methacrylic acids, maleic acids, and mixed polymers thereof, which can also contain small proportions of polymerizable substances having no carboxylic-acid functionality. The relative molecular weight of homopolymers of unsaturated carboxylic acids is generally between 5000 and 200,000, that of the copolymers between 2000 and 200,000, based in each case on free acid. Suitable compounds of this class are copolymers of acrylic acid or methacrylic acid with vinyl ethers, such as vinylmethyl ethers, vinyl esters, ethylene, propylene, and styrene, in which the proportion of acid is equal to at least 50 wt %. It is also possible to use, as water-soluble organic builder substances, terpolymers that contain two unsaturated acids and/or salts thereof as monomers and, as a third monomer, vinyl alcohol and/or a vinyl alcohol derivative or a carbohydrate. The first acid monomer or salt thereof may be derived from an ethylenically mono-unsaturated C3 to C8 carboxylic acid. The second acid monomer or salt thereof can be a derivative of a C4 to C8 dicarboxylic acid, for example maleic acid. The third monomeric unit is constituted by vinyl alcohol and/or an esterified vinyl alcohol. Polymers may contain 60 wt % to 95 wt %, in particular 70 wt % to 90 wt %, (meth)acrylic acid or (meth)acrylate, as well as 5 wt % to 40 wt % vinyl alcohol and/or vinyl acetate. Particular polymers are those in which the weight ratof (meth)acrylic acid respectively (meth)acrylate to maleic acid or maleate is between 1:1 and 4:1. Both the quantities and the weight ratios are based on the acids. The second acid monomer or salt thereof can also be a derivative of an allylsulfonic acid that is substituted in the 2-position with an alkyl radical, e.g. a C1 to C4 alkyl radical, or with an aromatic radical that may be derived from benzene or benzene derivatives. Terpolymers may contain 40 wt % to 60 wt %, in particular 45 to 55 wt %, (meth) acrylic acid or (meth)acrylate, particularly preferably acrylic acid or acrylate, 10 wt % to 30 wt %, by preference 15 wt % to 25 wt % methallylsulfonic acid or methallylsulfonate, and as a third monomer 15 wt % to 40 wt %, by preference 20 wt % to 40 wt % of a carbohydrate. This carbohydrate can be, for example, a mono-, di-, oligo-, or poly-saccharide, e.g. sucrose. The terpolymers generally have a relative molecular weight between 1000 and 200,000. Further copolymers include those that comprise, as monomers, acrolein and acrylic acid/acrylic acid salts, or vinyl acetate. Especially for the manufacture of liquid detergents, the organic builder substances can be used in the form of aqueous solutions, for example a 30- to 50-weight-percent aqueous solutions. All the aforesaid acids may be used in the form of their water-soluble salts, in particular their alkali salts.

Organic builder substances can be employed in quantities of up to 40 wt %.

Water-soluble inorganic builder materials include alkali silicates and polyphosphates, e.g. sodium triphosphate. Crystalline or amorphous alkali aluminosilicates, e.g. crystalline sodium aluminosilicates, may also be employed as water-insoluble, water-dispersible inorganic builder materials, in quantities of up to 50 wt %, for example. Aluminosilicates typically comprise particles having a particle size less than 30 [mu]m.

Crystalline alkali silicates may also be employed, either alone or used with amorphous silicates. The alkali silicates usable in consumer products of the present invention as detergency builders may have a molar ratof alkali oxide to $SiO_2$ below 0.95, in particular from 1:1.1 to 1:12, and can be present in amorphous or crystalline fashion. The alkali silicates may be sodium silicates, in particular the amorphous sodium silicates, having a $Na_2O:SiO_2$ molar ratfrom 1:2 to 1:2.8.

Builder substances may be contained in consumer product compositions according to the present invention at levels up to 60 wt %.

Peroxygen compounds include organic peracids or peracid salts of organic acids such as phthalimidopercapronic acid, perbenzoic acid, or salts of diperdodecanedioic acid, hydrogen peroxide, and inorganic salts that release hydrogen peroxide under application conditions, such as perborate, percarbonate, and/or persilicate. If solid peroxygen compounds are to be used, they can be utilized in the form of powders or granulates, which in principle can also be encased in known fashion.

Peroxygen compounds may be employed in amounts up to 50 wt %. The addition of small quantities of known bleaching-agent stabilizers, for example phosphonates, borates respectively metaborates, and metasilicates, as well as magnesium salts such as magnesium sulfate, may be useful.

Compounds that, under perhydrolysis conditions, yield aliphatic peroxocarboxylic acids having preferably 1 to 10 carbon atoms, in particular 2 to 4 carbon atoms, and/or (optionally substituted) perbenzoic acid, can be used as bleach activators. Substances that carry O- and/or N-acyl groups having the aforesaid number of carbon atoms, and/or optionally substituted benzoyl groups, are suitable. Multiple acylated alkylenediamines, in particular tetraacetylethylendiamine (TAED), acylated triazine derivatives, in particular 1,5-diacetyl-2,4-dioxohexahydro-1,3,5-triazine (DADHT), acylated glycolurils, in particular tetraacetyl glycoluril (TAGU), N-acylimides, in particular N-nonanoyl succinimide (NOSI), acylated phenolsulfonates, in particular n-nonanoyl or isononanoyl oxybenzenesulfonate (n- or iso-NOBS), carboxylic acid anhydrides, in particular phthalic acid anhydride, acylated polyvalent alcohols, in particular triacetin, ethylene glycol diacetate, 2,5-diacetoxy-2,5-dihydrofuran, and enol esters, as well as acetylated sorbitol and mannitol respectively mixtures thereof (SORMAN), acylated sugar derivatives, in particular pentaacetylglucose (PAG), pentaacetylfructose, tetraacetylxylose and octaacetyllactose, as well as acetylated, optionally N-alkylated glutamine and gluconolactone, and/or N-acylated lactams, for example N-benzoylcaprolactam, may be employed. Hydrophilically substituted acyl acetates and acyl lactams may likewise be employed. Combinations of conventional bleach activators can also be used. Such bleach activators can be contained in the usual quantity range, by preference in quantities from 1 wt % to 10 wt %, in particular 2 wt % to 8 wt %, based on the entire agent.

In addition to or instead of the aforementioned conventional bleach activators, sulfonimines and/or bleach-intensifying transition metal salts or transition metal complexes can also be contained as bleach catalysts. Included among the appropriate transition metal compounds are, in particular, salen complexes of manganese, iron, cobalt, ruthenium, or molybdenum and nitrogen-analog compounds thereof, carbonyl complexes of manganese, iron, cobalt, ruthenium, or molybdenum, complexes of manganese, iron, cobalt, ruthenium, molybdenum, titanium, vanadium, and copper having nitrogen-containing tripod ligands, amine complexes of cobalt, iron, copper, and ruthenium. Combinations of bleach activators and transition metal bleach catalysts can likewise be used. Bleach-intensifying transition metal complexes, in particular having the central atoms Mn, Fe, Co, Cu, Mo, V, Ti, and/or Ru, can be used in conventional quantities, such as up to 1 wt % based on the weight of the consumer product composition.

Suitable enzymes that may be employed in consumer product compositions are those from the class of the proteases, cutinases, amylases, pullulanases, hemicellulases, cellulases, lipases, oxidases, and peroxidases, as well as mixtures thereof. Enzymatically active substances recovered from fungi or bacteria, such as *Bacillus subtilis, Bacillus licheniformis, Streptomyces griseus, Humicola lanuginosa, Humicola insolens, Pseudomonas pseudoalcaligenes*, or *Pseudomonas cepacia*, are also suitable. The enzymes that are used as applicable can be adsorbed onto carrier substances and/or embedded into encasing substances in order to protect them from premature inactivation. They may be contained in washing products according to the present invention in amounts typically below 5 wt %.

Optical brighteners include derivatives of diaminostilbenedisulfonic acid or alkali metal salts thereof. Suitable, for example, are salts of 4,4'-bis(2-anilino-4-morpholino-1,3,5-triazinyl-6-amino)stilbene-2,2'-disulfonic acid, or compounds of similar structure that carry, instead of the morpholino group, a diethanolamino group, a methylamino group, an anilino group, or a 2-methoxyethylamino group. Brighteners of the substituted diphenylstyryl type can also be present, e.g. the alkali salts of 4,4'-bis(2-sulfostyryl) diphenyl, of 4,4'-bis(4-chloro-3-sulfostyryl)diphenyl, or of 4-(4-chlorostyryl)-4'-(2-sulfostyryl)diphenyl. Mixtures of the aforesaid optical brighteners can also be used.

Foam inhibitors include organopolysiloxanes and mixtures thereof with microfine, optionally silanated silicic acid, as well as paraffin waxes and mixtures thereof with silanated silicic acid or bis-fatty acid alkylenediamides. Mixtures of different foam inhibitors, for example those made of silicones, paraffins, or waxes, can also be employed. The foam inhibitors, in particular silicone- and/or paraffin-containing foam inhibitors are by preference bound to a granular carrier substance that is soluble or dispersible in water. Mixtures of paraffins and bistearylethylenediamide, in particular may be employed.

Soil release active substances are those compounds that positively influence the ability of oils and fats to be washed out of textiles. This effect becomes particularly apparent when the soiled textile is one that has already been previously washed several times with a washing agent according to the present invention that contains this oil- and fat-releasing component. The preferred oil- and fat-releasing components include, for example, nonionic cellulose ethers such as methyl cellulose and methylhydroxypropyl cellulose having a 15 to 30 wt % proportion of methoxy groups and a 1 to 15 wt % proportion of hydroxypropoxy groups, based in each case on the nonionic cellulose ethers, as well as polymers, known from the existing art, of phthalic acid and/or terephthalic acid resp. of their derivatives with monomeric and/or polymeric diols, in particular polymers of ethylene terephthalates and/or polyethylene glycol terephthalates or anionically and/or nonionically modified derivatives thereof.

Colour transfer inhibitors include polymers of vinylpyrrolidone, vinylimidazole, vinylpyridine-N-oxide, or copolymers thereof. Also usable are both polyvinylpyrrolidones having molecular weights from 15,000 to 50,000 and polyvinylpyrrolidones having molecular weights above 1,000,000, in particular from 1,500,000 to 4,000,000, N-vinyli midazole/N-vinyl pyrrol idone copolymers, polyvinyloxazolidones, copolymers based on vinyl monomers and carboxylic acid amides, pyrrolidone-group-containing polyesters and polyamides, grafted polyamidoamines and polyethylenimines, polymers having amide groups made up of secondary amines, polyamine-N-oxide polymers, polyvinyl alcohols, and copolymers based on acrylamidoalkenyl sulfonic acids. It is also possible, however, to use enzymatic systems encompassing a peroxidase and hydrogen peroxide or a substance that yields hydrogen peroxide in water.

Graying inhibitors are those materials that keep dirt that has been detached from the textile fibers suspended in a washing medium. Water-soluble colloids, usually organic in nature, are suitable for this, for example starch, size, gelatin, salts of ethercarboxylic or ethersulfonic acids of starch or of cellulose, or salts of acid sulfuric acid esters of cellulose or of starch. Water-soluble polyamides containing acid groups are also suitable for this purpose. Starch derivatives other than those recited above can also be used, for example aldehyde starches. Cellulose ethers such as carboxymethyl cellulose (sodium salt), methyl cellulose, hydroxyalkyl cellulose, and mixed ethers such as methylhydroxyethyl cellulose, methylhydroxypropyl cellulose, methylcarboxymethyl cellulose, and mixtures thereof may be used, for example in quantities from 0.1 to 5 wt % based on the weight of the consumer product.

Organic solvents include alcohols having 1 to 4 carbon atoms, in particular methanol, ethanol, isopropanol, and tert-butanol, diols having 2 to 4 carbon atoms, in particular ethylene glycol and propylene glycol, as well as mixtures thereof, and the ethers derivable from the aforesaid compound classes. Water-miscible solvents of this kind are present in washing products according to the present invention in amounts typically not exceeding 30 wt %.

pH regulators include citric acid, acetic acid, tartaric acid, malic acid, lactic acid, glycolic acid, succinic acid, glutaric acid, and/or adipic acid, but also mineral acids, in particular sulfuric acid, or bases, in particular ammonium hydroxides or alkali hydroxides. pH regulators of this kind are contained in the agents according to the present invention in quantities preferably not above 20 wt %, in particular from 1.2 wt % to 17 wt %.

The precursor of the present invention may be particularly used to perfume household products containing enzymes, such as those defined above, and in particular textile treatment products, such as detergents, containing enzymes.

The invention is now further described with reference to the following non-limiting examples. These examples are for the purpose of illustration only and it is understood that variations and modifications can be made by one skilled in the art.

EXAMPLE 1

Ethyl 2-acetyl-5-(4-isobutyl-2-methylphenyl)pent-2-enoate

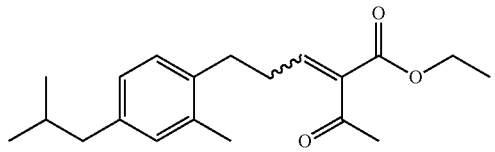 [SMILES: CCOC(=O)C(=CCCc1ccc(CC(C)C)cc1C)C(C)=O]

A mixture of 3-(4-isobutyl-2-methylphenyl)propanal (20.4 g, 100 mmol), ethyl acetoacetate (12.2 g, 94 mmol) and 2-methyl-2-amino 1-propanol (0.45 g, 5 mol %) was vigorously shaken until a homogeneous solution was formed, then left to stand in a closed bottle for 30 h. The now turbid mixture was diluted with MTBE, washed with brine/water (1:1), sat. aq. NaHCO₃, brine/water (1:1) and brine. The organic layer was dried (MgSO₄), filtered and the filtrate was concentrated. Residual traces of solvent were removed by drying at 0.1 mbar/50° C. for 1 h to yield 28.0 g (crude yield 88%) of a yellow oil containing 73% of ethyl 2-acetyl-5-(4-isobutyl-2-methylphenyl)pent-2-enoate as a mixture of E-/Z-isomers.

$^1$H NMR (CDCl$_3$, 400 MHz); sum of (E/Z) isomers: δ=7.22–6.74 (m, 4H), 4.49-4.15 (m, 2H), 2.85-2.75 (m, 1H), 2.69-2.53 (m, 1H), 2.50-2.40 (m, 2H), 2.37-2.20 (m, 8H), 1.95-1.82 (m, 1H), 1.40-1.28 (m, 3H), 0.95 and 0.94 (2d, J=6.6 Hz, together 6H) ppm. $^{13}$C-NMR (CDCl$_3$, 100 MHz); mixture of (E/Z) isomers: δ=200.7 (s), 194.9 (s), 166.1 (s), 164.2 (s), 147.5 (d), 147.2 (d), 139.7 (s), 137.2 (s), 135.5 (s), 135.2 (s), 131.0 (d), 128.5 (d), 128.2 (d), 126.7 (d), 61.0 (t), 60.9 (t), 44.9 (t), 44.8 (2t), 31.4 (t), 30.4 (t), 30.0 (t), 30.0 (d), 22.3 (q), 19.2 (q), 14.0 (q) ppm. MS (EI); major isomer: m/z (%)=316 (M$^+$, 2), 298 (1), 270 (5), 242 (5), 227 (4), 186 (7), 161 (100), 119 (38), 105 (14), 91 (10), 43 (37).

Odour description: floral green fatty muguet cyclamen, fatty buttery, green aldehydic, privet

EXAMPLE 2

4-Isobutyl-1-(4-(4-methoxyphenyl)but-3-en-1-yl)-2-methylbenzene

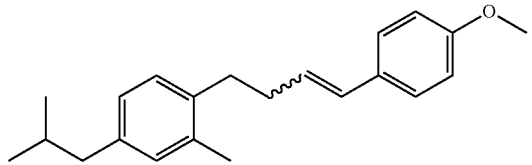 [SMILES: COc1ccc(C=CCCc2ccc(CC(C)C)cc2C)cc1]

Potassium t-butylat (1 M in THF, 9.1 mL) was added to a solution of (4-methoxybenzyl)-triphenylphosphonium bromide (4.21 g, 9.09 mmol) in THF (9 mL) at 0° C. After the red suspension was stirred at 0° C. for 10 min, 3-(4-isobutyl-2-methylphenyl)propanal (2.04 g, 10.0 mmol) in THF (5 mL) was added at 0° C., and the mixture was stirred at 25° C. for 2 h. After addition of water, the aqueous layer was extracted with hexane (2×). The combined organic phases were washed with MeOH/water (4:1; 3×), dried (MgSO₄), filtered and the filtrate was concentrated. The residue was purified by flash chromatography on SiO₂ (hexane/EtOAc 199:1→99:1) and dried in the "Kugelrohr" oven under HV to yield 1.16 g (41%, purity 99%) of the title compound as a colorless oil. The product consists of a mixture of E-/Z-isomers (ratio 1.8:1).

$^1$H NMR (CDCl$_3$, 400 MHz); mixture of (E/Z) isomers: δ=7.33–7.30 (m, 2H), 7.24-7.20 (m, 2H), 7.12 (d, J=7.3 Hz, 1H), 7.09 (d, J=7.6 Hz, 1H), 6.98-6.94 (m, 4H), 6.90-6.86 (m, 4H), 6.43 (dt, J=11.5, 1.7 Hz, 1H), 6.42 (d, J=15.9 Hz, 1H), 6.20 (dt, J=15.9, 6.9 Hz, 1H), 5.69 (dt, J=11.7, 7.1 Hz, 1H), 3.84 (s, 3H), 3.84 (s, 3H), 2.79-2.74 (m, 4H), 2.67-2.60 (m, 2H), 2.52-2.47 (m, 2H), 2.46 (d, J=7.1 Hz, 2H), 2.45 (d, J=7.1 Hz, 2H), 2.35 (s, 3H), 2.31 (s, 3H), 1.89 (nonet, J=6.9 Hz, 1H), 1.88 (nonet, J=6.9 Hz, 1H), 0.95 (d, J=6.6 Hz, 6H), 0.94 (d, J=6.6 Hz, 6H) ppm. $^{13}$C-NMR (CDCl$_3$, 100 MHz); mixture of (E/Z) isomers: δ=158.7 (s), 158.2 (s), 139.3 (s), 139.3 (s), 137.2 (s), 137.1 (s), 135.5 (s), 135.4 (s), 131.0 (2d), 130.6 (d), 130.5 (d), 130.3 (s), 129.9 (2d), 129.5 (d), 128.7 (d), 128.5 (d), 128.5 (d), 128.1 (d), 127.0 (2d), 126.6 (d), 126.6 (d), 113.9 (2d), 113.5 (2d), 55.2 (q), 55.2 (q), 45.0 (t), 45.0 (t) 33.7 (t), 33.1 (t), 33.0 (t), 30.2 (2d), 29.3 (t), 22.4

(4q), 19.4 (2q) ppm. MS (EI); Z-isomer: m/z (%)=308 (M+·, 3), 161 (6), 148 (11), 147 (100), 131 (3), 119 (8), 118 (7), 117 (6), 115 (8), 103 (4), 91 (11), 43 (4); E-isomer: m/z (%)=308 (M+·, 3), 161 (5), 148 (11), 147 (100), 131 (3), 119 (8), 118 (7), 117 (6), 115 (8), 103 (4), 91 (10), 43 (3).

Odour description: floral muguet, green fatty cyclamen, floral fruity mimosa

The invention claimed is:

1. A fragrance precursor according to the formula 1

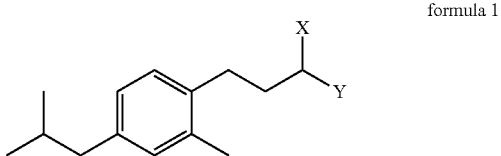

formula 1 wherein

X and Y together represent a double bond to a carbon atom bearing $R_1$ and $R_2$, $R_1$ is H, methyl, acetyl or $C_1$-$C_3$ alkoxy carbonyl, and $R_2$ is phenyl optionally substituted with up to 3 groups selected from $C_1$-$C_4$ alkyl, vinyl, hydroxy, $C_1$-$C_3$ alkoxy, and —O—$CH_2$—O—, or $R_2$ is naphthyl, (naphthyl)methyl, 1,1,2,4,4,8-hexamethyl-1,2,3,4-tetrahydronaphthalen-7-yl, or 1,1,2,4,4,-pentamethyl-1,2,3,4-tetrahydronaphthalen-7-yl or $R_2$ is $COR_3$, wherein $R_3$ is H, $C_1$-$C_{10}$ alkoxy, or $C_1$-$C_4$ alkyl;

or wherein

X is $OR_4$, wherein $R_4$ is H or alkyl, and

Y is $OR_5$, wherein $R_5$ is alkyl.

2. A fragrance precursor according to claim 1 selected from the group consisting of:
   ethyl 2-acetyl-5-(4-isobutyl-2-methylphenyl)pent-2-enoate, and
   4-isobutyl-1-(4-(4-methoxyphenyl)but-3-en-l-yl)-2-methylbenzene.

3. A perfume composition comprising a fragrance precursor according to claim 2.

4. The perfume ingredient according to claim 3 which is adapted to release an ingredient with muguet odour characteristics.

5. A perfume composition comprising a fragrance precursor according to claim 2.

6. A personal care or household care composition comprising a fragrance precursor according to claim 2.

7. A method of imparting a muguet odour characteristic to a perfume composition comprising the step of: adding to said composition at least a fragrance precursor according to claim 2.

8. A perfume ingredient comprising a fragrance precursor according to claim 1.

9. The perfume ingredient according to claim 8 which is adapted to release an ingredient with muguet odour characteristics.

10. A perfume composition comprising a fragrance precursor according to claim 1.

11. A perfume composition according to claim 10 that is free of aryl-substituted propanals, that are unsubstituted on the aryl ring at a position ortho to the substituent bearing the aldehyde functionality.

12. A perfume composition according to claim 10 which further comprises 3-(4-isobutyl-2-methylphenyl) propanal.

13. A perfume composition according to claim 10 comprising one or more additional fragrance ingredients.

14. A perfume composition according to claim 10, which is adapted to release an ingredient with muguet odour characteristics.

15. A personal care or household care composition comprising a fragrance precursor according to claim 1.

16. A method of imparting a muguet odour characteristic to a perfume composition comprising the step of: adding to said composition at least a fragrance precursor according to claim 1.

17. The fragrance precursor of claim 1, wherein $R_2$ is benzo[d][1,3]dioxo-5-yl, 4-methylphenyl, 4-methoxyphenyl, 4-vinylphenyl or 3-ethoxy-4-hydroxyphenyl.

18. The fragrance precursor of claim 1, wherein $R_2$ is formyl, acetyl, ethoxycarbonyl, or 1-(3,3-dimethylcyclohexyl)ethoxycarbonyl.

* * * * *